United States Patent [19]
Lacey et al.

[11] Patent Number: 5,793,480
[45] Date of Patent: Aug. 11, 1998

[54] COMBINED INTERFEROMETER/ ELLIPSOMETER FOR MEASURING SMALL SPACINGS

[75] Inventors: Christopher A. Lacey; Kenneth H. Womack; Carlos Duran; Ed Ross; Semyon Nodelman, all of San Diego, Calif.

[73] Assignee: Phase Metrics, Inc., San Diego, Calif.

[21] Appl. No.: 719,003

[22] Filed: Sep. 24, 1996

Related U.S. Application Data

[63] Continuation-in-part of Ser. No. 522,553, Sep. 1, 1995, Pat. No. 5,638,178.
[51] Int. Cl.$^6$ ............................... G01B 9/02; G01N 21/21
[52] U.S. Cl. .................... 356/73; 356/357; 356/369
[58] Field of Search .................................. 356/367, 369, 356/357, 364, 73

[56] References Cited

U.S. PATENT DOCUMENTS

| | | | |
|---|---|---|---|
| 3,985,447 | 10/1976 | Aspnes | 356/369 |
| 4,346,996 | 8/1982 | Miller . | |
| 5,280,340 | 1/1994 | Lacey | 356/357 |
| 5,557,399 | 9/1996 | de Groot | 356/357 |

Primary Examiner—Richard A. Rosenberger
Attorney, Agent, or Firm—Blakely Sokoloff Taylor & Zafman

[57] ABSTRACT

An apparatus and method for measuring the space between a transparent member such as a substrate, and reflective member such as a slider. The apparatus includes a first optical system which detects a first light beam that is reflected from the substrate and the slider. The reflected light is separated into four separate beams. The intensities of the beams are detected and utilized to determine a first stokes parameter, a second stokes parameter, a third stokes parameter and a fourth stokes parameter of the reflected light. The stokes parameters are used to compute the real index of refraction n, extinction coefficient k and the thickness of the space. The four stokes parameters account for any depolarized light that is reflected from the slider. The first optical system may have a photodetector which detects an image of the slider. The image provides multiple data points that can be used to calculate n, k and the thickness of the air gap without a retract routine. The apparatus may also have a second optical system which detects a second light beam reflected from the substrate and the slider. The second optical system can be used to dynamically measure a thickness of the space. In the combined system the first optical system may accurately measure the n and k of a slider area while the second optical system dynamically measures the thickness of the air gap.

10 Claims, 4 Drawing Sheets

COMBINED INTERFEROMETER/ELLIPSOMETER FOR MEASURING SMALL SPACINGS

This application is a continuation-in-part of Ser. No. 522,553 filed on Sep. 1, 1995, now U.S. Pat. No. 5,638,178.

BACKGROUND OF THE INVENTION

1. Field of the Invention

The present invention relates to an instrument for measuring the space between a transparent member and a reflective member.

2. Description of Related Art

Hard disk drives contain a magnetic transducer(s) that magnetizes a flat rotating disk. The magnetic transducer is typically assembled to a suspension arm as part of a head gimbal assembly (HGA) that is suspended from an actuator arm. The actuator arm has a motor that moves the slider across the disk surface. Rotation of the disk creates an airstream which lifts the slider off of the disk surface. The air bearing created by the rotating disk prevents the slider and disk material from structurally wearing. The thickness of the air bearing can vary depending upon the spring rate of the suspension arm, aerodynamic characteristics of the slider and other factors.

When mass producing hard disk drives, it is desirable to measure the air bearing for each HGA to insure that the air bearing thickness is within operational tolerances. Various optical systems have been developed to detect the microinch and submicroinch air bearing thicknesses typically created in hard disk drive units. The air bearing thickness can be measured in optical systems by inserting the suspension arm into a test unit which has a transparent glass substrate. A light beam is then directed through the glass substrate and onto the slider. The reflection of light from the slider and the substrate air bearing interface creates an interference pattern that is detected by a photodetector. The thickness of the air bearing is computed from the interference pattern. The light source and photodetector are typically at approximately normal incidence to the slider and transparent substrate.

Interferometric testers typically require a calibration procedure to determine the maxima and minima of the interference pattern. The maxima and minima may be determined by varying the air bearing thicknesses, either by changing the rotational speed of the disk, or by mechanically unloading the slider in a retract routin calibration. Once the maxima and minima are known, the air bearing thickness associated with a given detector signal can be calculated from the known functional form of the multiple-beam interference.

It has been found that some slider designs do not produce a wide enough range of air bearing thicknesses in response to variations in disk speed to determine maxima and minima. Retraction by mechanically unloading the slider has also been found to introduce errors because of slider tilt. In addition, the rate of change of light intensity goes to zero when the air bearing thickness is varied through an interference minimum or maximum. Additionally, it has been found that the signal to noise ratio degrades as the slider approaches the minimum associated with slider to disk contact.

For these reasons, prior art interferometers, such as the Phase Metrics DFHT, incorporate multiple wavelengths, and corresponding multiple detectors for signal to noise ratio improvements and for coping with loss of flying height measurement sensitivity at spacings which correspond to interferometric maxima and minima. A second type of multiple wavelength tester was marketed by IBM under the trademark CRAMA. The CRAMA system uses a two dimensional detector array in combination with a least square fit computation process to recover phase and determine air bearing thickness at each pixel of the interferogram image.

U.S. Pat. No. 5,218,424 issued to Sommargren, discloses an interferometer that functions at an incident angle that is not normal to the substrate. The Sommargren tester generates two laterally displaced perpendicularly polarized coherent light beams that are directed through the glass substrate at Brewster's angle for the substrate-air interface. One of the polarized light beams is transmitted through the substrate and reflected off of the slider. The other beam is reflected from the glass-air bearing interface. The reflected polarized light beams are recombined and directed onto a two-dimensional photodetector array. The Sommargren system includes a phase shifter that shifts the phase of the polarized beams directed onto the substrate. The detector measures the relative phase difference between the light reflected from the slider and the substrate-air bearing interface. The air bearing thickness is proportional to the phase difference of the light beams.

The Sommargren technique is advantageous because a calibration technique is not required to detect the maxima and minima for an interference signal. Additionally, intensity sensitivity is uniform and does not approach zero at the maximum and minimum locations. Unfortunately the Sommargren system will not compensate for variations in the real index of refraction n and extinction coefficient k of the slider. These coefficients may vary from slider to slider. Any variation in n and k will degrade the accuracy of the test results.

To improve the accuracy of the flying height tester the sliders are typically measured with an ellipsometer to determine the real index of refraction n and extinction coefficient k. The measured n and k values are then manually entered into the computer of the flying height tester to be used in computing the gap of the air bearing. Separately measuring the n and k values increases the time required to test the sliders.

There has been marketed a flying height tester by Zygo Corp. which measures the ellipsometric parameters $\Psi$ and $\Delta$ and utilizes the measured parameters to calculate n, k and the thickness of the air bearing. In the Zygo system the reflected light is separated into two orthogonal polarization components p and s. The system has a receiver which measures the intensities of the two polarization components and the phase angle between the components. The Zygo flying height tester does not account for light that is depolarized and thus does not accurately calculate the real index of refraction n and extinction coefficient k of the slider. Additionally, it is believed that the Zygo tester must utilize a retract routine to measure n, k and the gap of the air bearing. It would therefore be desirable to provide a flying height tester that will account for the depolarized light reflected from the slider. It would also be desirable to measure n, k and the air bearing thickness without a retract routine.

Additionally, magnetoresistive (MR) recording heads are typically constructed with thin film processes, wherein the MR element is embedded within a layer of aluminum oxide. The aluminum oxide is relatively translucent such that the n and k values of the head in the area of the MR element are different than the index n and extinction coefficient k in the remaining portions of the head. For this reason flying height testers typically reflect the light beam off of the rails on the air bearing surface. The rails are located away from the MR elements in the trailing edge of the slider. It is difficult to determine the flying height at the region of the slider transducer because of the variations in the index along the surface of the slider.

To determine the reliability of the head it is desirable to measure the minimum gap of the air bearing. The minimum air gap is typically located at the trailing edge of the slider. By reflecting the light beam off of the rails and not the trailing edge, the flying height testers of the prior art do not determine the true minimum air gap of the air bearing. It would therefore be desirable to provide a flying height tester that can accurately measure n, k and the minimum air bearing gap. To minimize the time required to test a part, it would be desirable to measure n, k and the air gap without a retract routine. It would also be desirable to provide a flying height tester that can provide an image of the slider to determine various hydrodynamic characteristics of the head.

SUMMARY OF THE INVENTION

The present invention is an apparatus and method for measuring the space between a transparent member such as a substrate, and reflective member such as a slider. The apparatus includes a first optical system which detects a first light beam that is reflected from the substrate and the slider. The reflected light is separated into four separate beams. The intensities of the beams are detected and utilized to determine a first stokes parameter, a second stokes parameter, a third stokes parameter and a fourth stokes parameter of the reflected light. The stokes parameters are used to compute the real index of refraction n, extinction coefficient k and the thickness of the space. The four stokes parameters account for any depolarized light that is reflected from the slider. The first optical system may have a photodetector that detects an image of the slider. The image provides multiple data points that can be used to calculate n, k and the thickness of the air gap without a retract routine. The apparatus may also have a second optical system which detects a second light beam reflected from the substrate and the slider. The second optical system can be used to dynamically measure a thickness of the space. In the combined system the first optical system may measure the n and k of a slider while the second optical system dynamically measures the thickness of the air gap.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
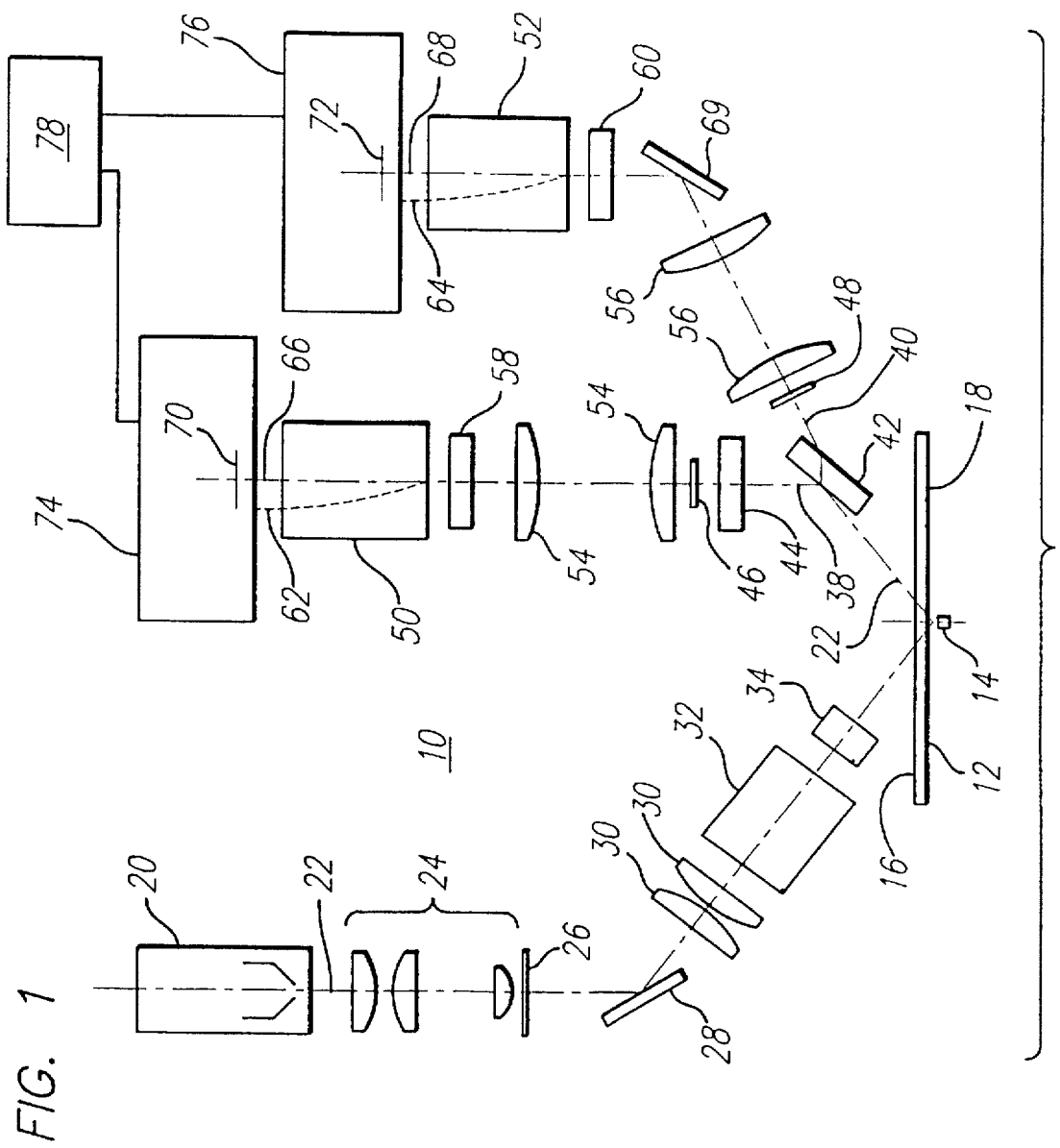
FIG. 1 is a schematic of a polarimeter detection system of the present invention.

Referring to the drawings more particularly by reference numbers, FIG. 1 shows a polarimeter detection system 10 of the present invention. The detection system 10 is used to measure the space between a transparent member 12 and a reflective member 14. The transparent member has a top surface 16 and a bottom surface 18.

The transparent member 12 is preferably a glass disk that is mounted to a motor (not shown) which can rotate the disk. The reflective member 14 is preferably a slider that contains a magnetic transducer which magnetizes and senses the magnetic field of a magnetic disk. The slider is typically mounted to a suspension arm (not shown). When the disk is rotated the airstream created by the rotating disk creates a pressure which pushes the slider away from the disk surface. The gap between the disk and slider is referred to as an air bearing. Although measuring the thickness of an air bearing of a hard disk drive assembly is shown and described, it is to be understood that the present invention can be used to determine the thickness of other substrates and layers.

The system 10 includes a light source 20 which emits a beam of light 22. In the preferred embodiment, the light source 20 is a Xenon arc strobe, halogen lamp or a laser diode(s). The light beam 22 is directed through a condenser assembly 24 and an aperture 26. Because most slider designs are rectangular in shape it is desirable to have a rectangularly shaped aperture 26, although it is to be understood that the aperture 26 may have other shapes.

The light beam 22 is reflected by a mirror 28 into lenses 30. The lenses 30 focus the light beam 22 onto a small portion of the slider 14. The focused light should be preferably small enough to prevent interference between the light reflected from the slider 14 and light reflected from the top surface 16 of the disk 12.

The focused light beam goes through a crystal polarizer 32 and a quarter waveplate retarder 34. The polarizer 32 polarizes the light beam and the quarter waveplate 34 retards a polarized component to produce a circularly polarized light beam. Although a separate polarizer 32 and quarter waveplate 34 are shown and described, it is to be understood that other elements for circularly polarizing the light may be employed. Additionally, although circularly polarized light is discussed, the present invention may use a light beam polarized in another manner, such as 45° linearly polarized light.

Figure 2:
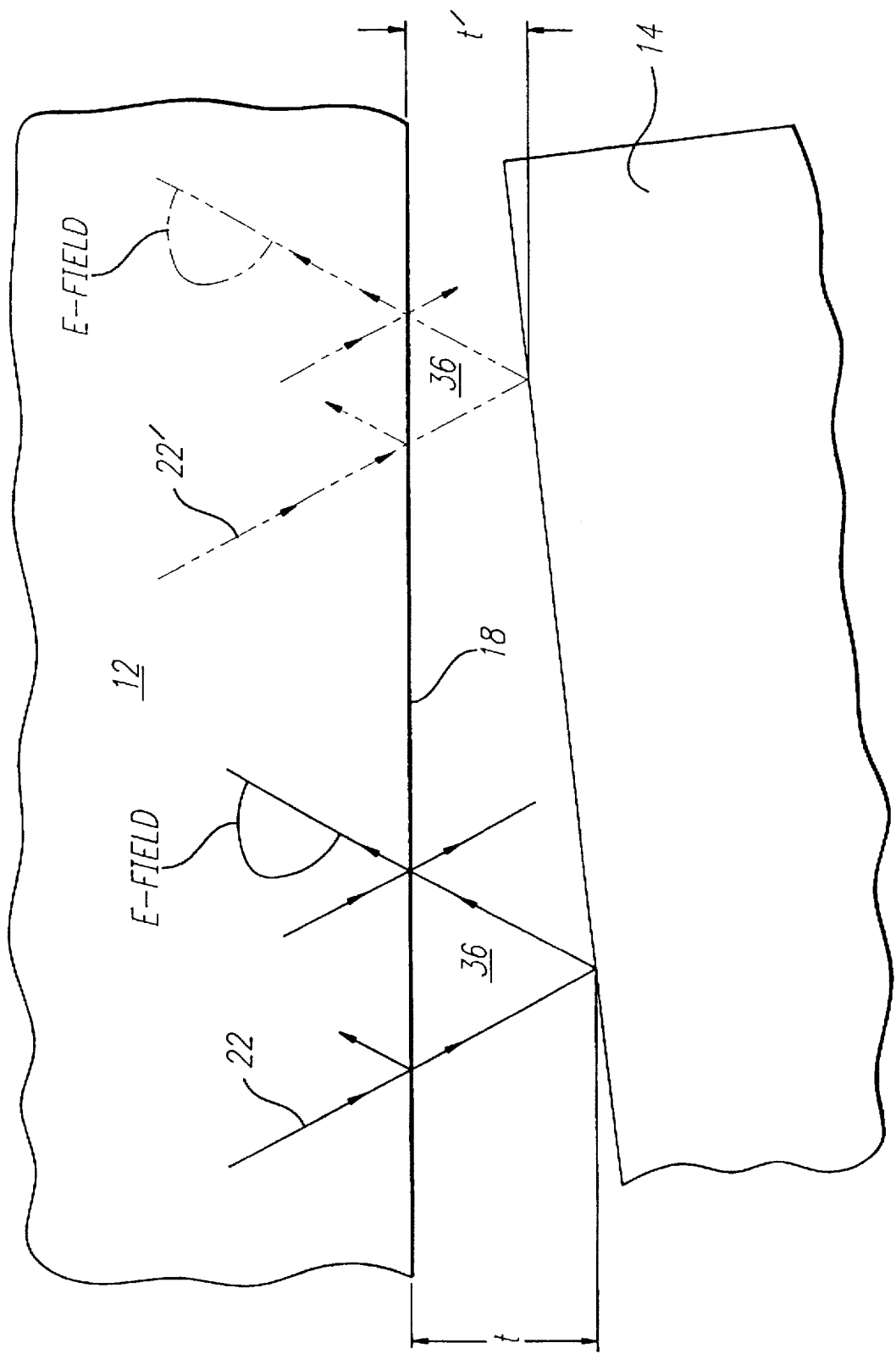
FIG. 2 is an enlarged view showing a light beam reflected from a slider-substrate interface.

As shown in FIG. 2, the circularly polarized light beam 22 is directed onto the substrate 12. In the preferred embodiment the polarized light beam has an angle of incidence of approximately 60°. The light refracts through the substrate 12, and the space 36 between the bottom surface 18 of the substrate and the slider 14. The space 36 has a thickness of t. The light beam 22 then reflects off of the slider 14 and back through the space 36 and substrate 12. The slider 14 has a complex index of refraction which is the summation of the real index of refraction n and the extinction coefficient k.

When the light beam 22 reflects off of a slider 14 located at space thickness t the reflected light has a certain E-field polarization shown in solid lines. When the light beam is reflected from a space thickness t' the optical path becomes longer, so that the phase of the polarized reflected light beam 22' is different, as indicated in phantom, than the reflected light beam 22. In general, the polarization of the light beam 22 will be a function of the space thickness and the optical properties of the substrate 12 and the slider 14. The varying space thickness t' can be created by varying the disk speed and the corresponding spacing of the air bearing, or by measuring a different point on the slider by analyzing a different group of pixels on the CCDs.

Referring to FIG. 1, the reflected light beam is split into two light beams 38 and 40 by a beam splitter 42 which reflects a portion of the reflected light and transmits a portion of the light. In the preferred embodiment, the beam splitter 42 is constructed from a BK-7 glass that has a coating of $TiO_2$ with an index of refraction of 2.35 and a thickness of 28.5±3 nm.

Beam 38 is reflected from the beam splitter 42 to substrate 44. The substrate 44 emulates the transmissivity of the beam splitter 42. Both beams 38 and 40 travel through a pair of crystal quartz 45° polarization rotators 46 and 48. The polarization rotators 46 and 48 vary the polarization of the light beams 38 and 40 to orient the polarization vectors to optimize the usage of the polarization prisms 50 and 52.

The polarized light beams 38 and 40 are focused onto a pair of polarization displacement prisms 50 and 52 by lenses 54 and 56. The light beams are filtered by a pair of interference filters 58 and 60 before traveling into the prisms 50 and 52, respectively. In the preferred embodiment, the interference filters 58 and 60 have a bandwidth of 10 nm centered at 546 nm.

Each polarization displacement prism laterally displaces one polarization component of a polarized beam 38 and 40 from another polarization component of the polarized beam. The different polarized components define a pair of extraordinary beams 62 and 64 that are spatially displaced from a pair of ordinary beams 66 and 68, respectively. Each beam 62, 64, 66 and 68 will have a different polarization and typically a different corresponding light intensity than the other beams. Although the extraordinary beams 62 and 64 are shown, it is to be understood that the beams typically bend in a plane perpendicular to the paper. The beams are shown in the manner depicted in FIG. 1 for purposes of clarity. The displacement prisms 50 and 52 may be a Wollaston prism or any other birefringent polarizer. The size of the system 10 may be reduced by bending the beam 40 with a mirror 69.

The intensities of the light beams 62, 64, 66 and 68 are detected by charged coupled devices (CCD) 70 and 72 located within cameras 74 and 76. Although a camera is described, it is to be understood that any photodetector may be implemented. There is typically a separate CCD for each light beam 62, 64, 66 and 68. The CCD devices 70 and 72 convert the light energy of the beams 62, 64, 66 and 68 into electrical signals. The electrical signals are provided to a processor 78 that is coupled to the cameras 74 and 76.

The four beams 62, 64, 66 and 68 produce four electrical detection signals defined by the equation.

$$J_i = (J_1, J_2, J_3, J_4)^T \quad (1)$$

where;

$J_i = C_i I_i$ $C_i$ = the sensitivity of the detectors.

$I_i$ = the intensity of the light beams.

From the detection signal the Stokes parameters Si representing the polarization of the light reflected from the slider can be computed with the following transformation matrix:

$$S_i = F^{-1} J_i \quad (2)$$

where;

$F^{-1}$ = is an instrument characteristic matrix of the tester.

From the Stokes parameters the ellipsometric parameters delta (Δ) and psi (Ψ) can be calculated using the equations:

$$\tan\Psi = \left[ \frac{S_0 - S_1}{S_0 + S_1} \right]^{.5} \quad (3)$$

$$\tan\Delta = \frac{S_2}{S_3} \quad (4)$$

where;

$S_0, S_1, S_2, S_3$ = the Stokes parameters.

The ellipsometric parameters delta Δ and psi Ψ are a function of the unknown space thickness t, the real index of refraction n, the extinction coefficient k of a given slider and other known optical parameters such as the index of the glass and air. Because there are two equations and three unknowns, it is preferably to measure the light intensities and compute the ellipsometric parameters for two separate space thicknesses $t_1$ and $t_2$. The measurements at each thickness $t_1$ and $t_2$ produce four known values; $\Delta_1$, $\Delta_2$, $\Psi_1$ and $\Psi_2$. The four known values are used to compute the four unknown values; $t_1$, $t_2$, n and k. The four unknowns values are preferably computed from the four known values using a Newton's method with numerical derivatives.

In the preferred embodiment it is desirable to limit the spacing to one periodic cycle. If the spacing is above one periodic cycle an integral number of periods can be added to the result to provide the correct spacing. More than two spacings can be simultaneously analyzed using a least squares or other technique to reduce the data for the overdetermined problem.

What is thus provided is an optical system for measuring the spacing of a thin layer or substrate without restricting the angle of incidence of the reflected light beam. Additionally, the present invention does not require the maxima and minima calibration steps typically found in interferometers of the prior art.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. For example, instead of splitting the reflected beam into four separately polarized beams, the reflected light beam could be directed into a rotating polarization retarder followed by a fixed polarizer. The intensity of the beam transmitted to the detector is changed at predetermined time intervals because of the rotation of the retarder. The light intensity of the beam may be measured at the different time intervals and used to compute the Stokes parameters and the corresponding t, n and k values of the glass-slider interface. In addition, instead of measuring delta and psi at multiple spacings, the ellipsometric parameters could be measured by using multiple angles of incidence, or multiple wavelengths of light to determine t, n and k. Furthermore, the system may contain only three separate photodetectors.

Figure 3:
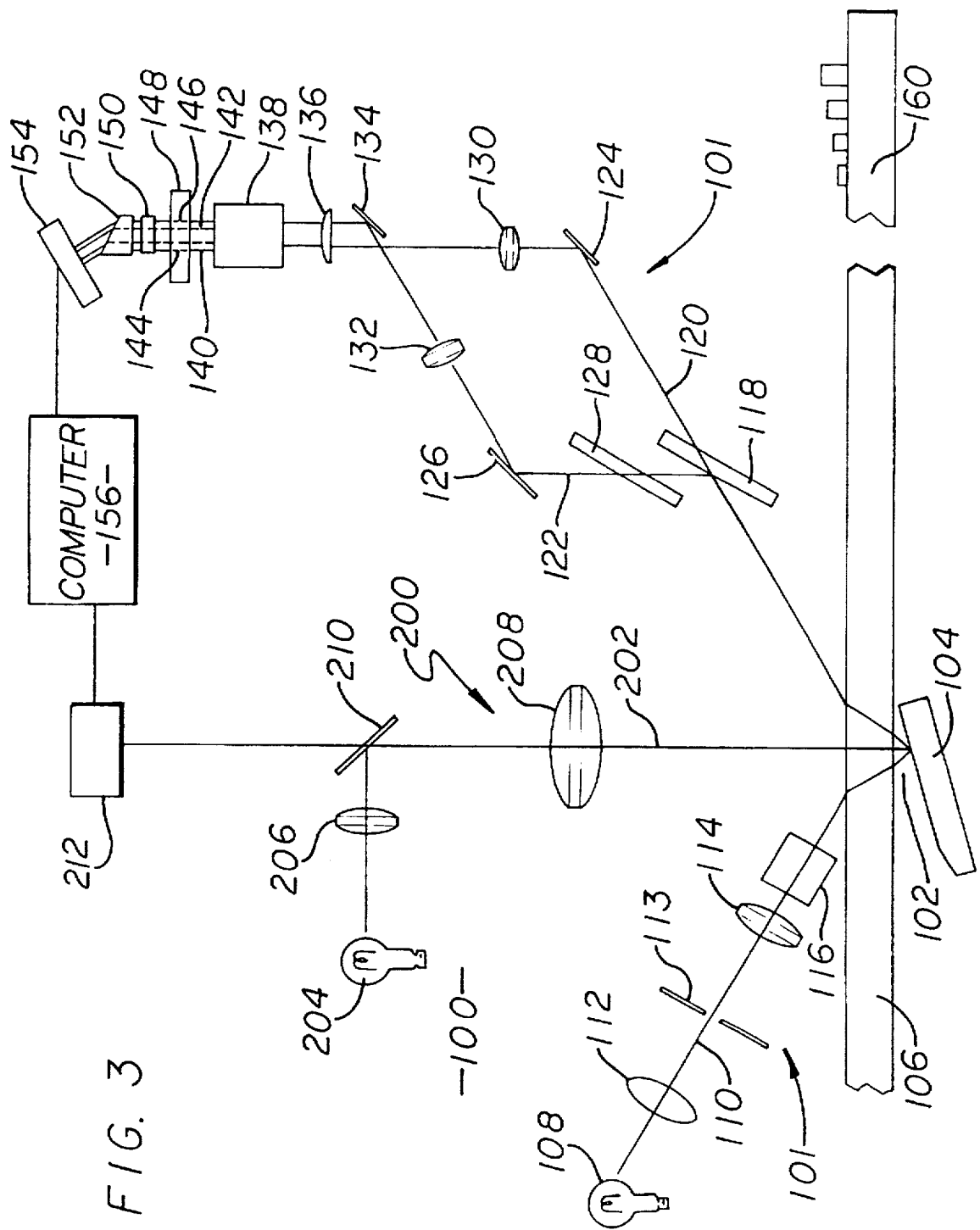
FIG. 3 is a schematic of an alternate embodiment of the detection system.

FIG. 3 shows an alternate embodiment of a system 100 for measuring the gap of the air bearing 102 between a slider 104 and a transparent substrate 106. The system 100 includes a first optical system 101 which has a light source 108 that generates a first beam of light 110. The light source 108 is preferably a quartz halogen lamp, although other light sources as laser diodes may be implemented. The light source 108 should have a coherence length that is relatively long compared to the air bearing gap and short compared to the lenses of the optical system. The coherence length can be reduced by placing a rotating diffuser in the light path. The coherence length should be in the range of 1 to 1000 microns.

A lens 112 directs the light 110 through a field stop 113. The field stop 113 is imaged onto the slider 102 by lens 114. The imaged light is polarized at 45° by a calcite polarizer 116. The light 110 is reflected from the substrate 106 and the slider 104. A beam splitter 118 splits the reflected light into two different beams 120 and 122. The beam splitter 118 is coated to provide maximum detection signals.

The beams 120 and 122 are reflected off of mirrors 124 and 126. Optical window 128 compensates for the additional optical path of the beam splitter substrate 118. The beams 120 and 122 are directed through lenses 130 and 132 and reflected off of mirror 134.

The beams 120 and 122 are directed through a polarization rotator 136 and then through a polarization beam displacer 138 which creates a pair of ordinary beams 140 and 142 and a pair of extraordinary beams 144 and 146. The extraordinary beams 144 and 146 are displaced in a direction perpendicular to the plane of the drawing. The four beams 140, 142, 144 and 146 pass through an interference filter 148. The interference filter 148 preferably has a 10 nm bandpass which is centered at 546 nm. The extraordinary beams 144 and 146 pass through a focus compensator 150 which compensates for the different optical paths of the ordinary and extraordinary beams through the displacer 138. The beams 140, 142, 144 and 146 pass through prism 152 which compensates for aberrations created by the substrate 106, beam splitter 118 and window 128.

The four beams 140, 142, 144 and 146 are detected by a photodetector 154. The four beams contain different polarization states of the reflected light. The detector 154 is preferably a charged coupled device (CCD) camera that can detect two-dimensional images of the slider 104. Each beam 140, 142, 144 and 146 provides an image of the slider 104. The different beams are detected on different areas of the camera 154. Although a CCD camera is described, it is to be understood that the detector 154 may be any two dimensional optoelectronic detector array. The light source and detector should be capable of rapid image acquisition.

The camera 154 is coupled to a computer 156 that computes the real index of refraction n and extinction coefficient k of the slider 104 from the light intensities measured by the detector 154. The beam spot of the first optical system 101 is large enough to cover the entire air bearing surface of the slider. The computer 156 preferably computes a stokes vector for each point of the slider image from the measured intensities and the predetermined instrument matrix utilizing equation (2). The index n, coefficient k and air bearing thickness can then be computed from the stokes vectors. Because sliders fly at an angle, the air bearing has a varying thickness along the length of the air bearing surface. Additionally, sliders typically have a crown which also varies the thickness of the air bearing. The varying thicknesses are sensed by providing multiple data points which can be used to compute n, k and the thickness of the air gap without a retract routine or moving the light beam of the system.

The image also allows for the computation of the air bearing thickness, n and k, and both the pitch and roll of the slider. For example, 100 different points of the image will provide 100 sets of stokes vectors. A simplex optimization scheme (Numerical Recipes in C) can be utilized to determine the best fit of the 5 unknowns with the stokes vectors to determine thickness, pitch, roll, n and k. Assumption, such as a flat slider, can be utilized to simplify the computation, although the method is extendible to determine slider curvature and warping and varying n and k values in different regions of the slider. Knowing the n and k for each area of the slider would allow the tester to reflect light from the trailing edge of the slider and measure the minimum gap of the air bearing. The tester can also more accurately determine the flying height of the full slider surface, including the region of the slider transducer.

The instrument characteristic matrix $F^{-1}$ used to determine the stokes vectors from the measured intensities is typically a 4 by 4 matrix that contains 16 unknowns. The system 100 must be calibrated to determine the unknowns. The system 100 may be calibrated by directing the light beam 110 onto a calibration medium 160 to compute the unknowns of the instrument characteristic matrix $F^{-1}$ for each pixel.

Figure 4:
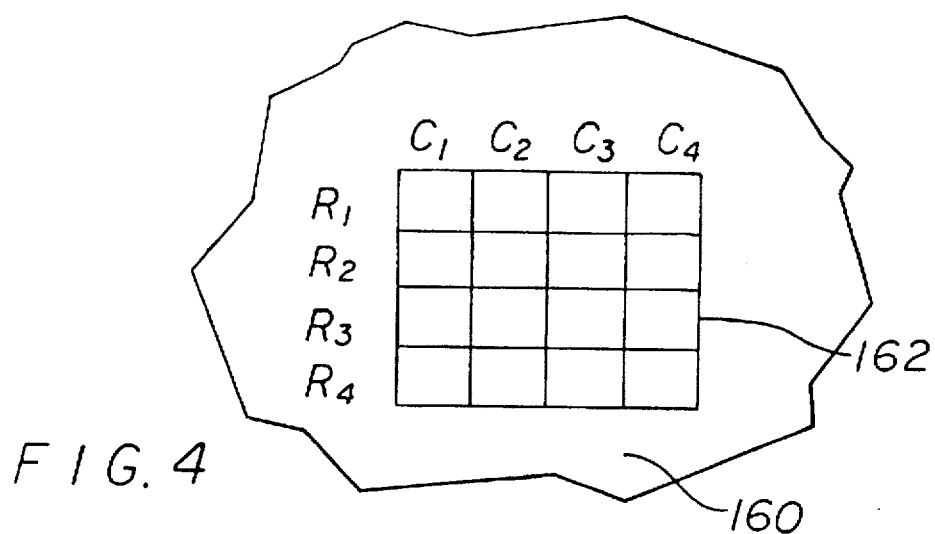
FIG. 4 is a top view of a calibration medium for the system of FIG. 3.

As shown in FIG. 4 the medium 160 may contain 16 different regions 162 arranged into four different rows $R_{1-4}$ and four different columns $C_{1-4}$. Each region 162 has a different thickness that corresponds to a specific air bearing thickness. The regions 162 can be constructed using a first coating of metal oxide with an index of refraction of 2 at 550 nm. In the preferred embodiment the first coating is a compound sold by Merck Corporation under the part designation H4. A second coating is then applied to the first coating. The second coating may be silicon dioxide $SiO_2$ which has an index of refraction of 1.46 at 550 nm.

The medium 160 may be constructed with 5 separate coating steps. The first coating is initially applied by covering three columns of the array and coating the remaining exposed column to the appropriate thickness. This process is repeated for three different columns. The first column $C_1$ has no coating. The second column $C_2$ is coated with H4 to a thickness of 47.5 nm, the third column $C_3$ is coated to a thickness of 69.5 nm and the fourth column $C_4$ is coated to a thickness of 94 nm. The second coating is then applied to the array. The first row $R_1$ is not coated. The second row $R_2$ is coated with 127 nm of $SiO_2$ and the fourth row $R_4$ is coated with 60 nm of $SiO_2$. The third row $R_3$ is coated during the coating of rows R2 and R4 for a $SiO_2$ thickness of 187 nm. Each region 162 is designed to effect the polarization state of a light beam reflected from the medium 160 to obtain multiple stokes parameter data.

The system 100 is calibrated by reflecting the light beam 110 from each region 162 and measuring the intensities of the four beams 140, 142, 144 and 146. Measurements for all 16 regions 162 are stored to compute the 16 unknowns of the instrument characteristic matrix $F^{-1}$. An instrument characteristic matrix is computed for each pixel of the two dimensional detector and stored into the computer. The optical system can be mounted to a gantry which can move the light beam 110 to reflect from each ridge 162 of the medium 160. As an alternate embodiment the ridges 162 may be formed on a medium (not shown) that replaces the existing substrate 106 of the system. After the system is calibrated the calibration medium is replaced with the test substrate 106.

Figure 5:
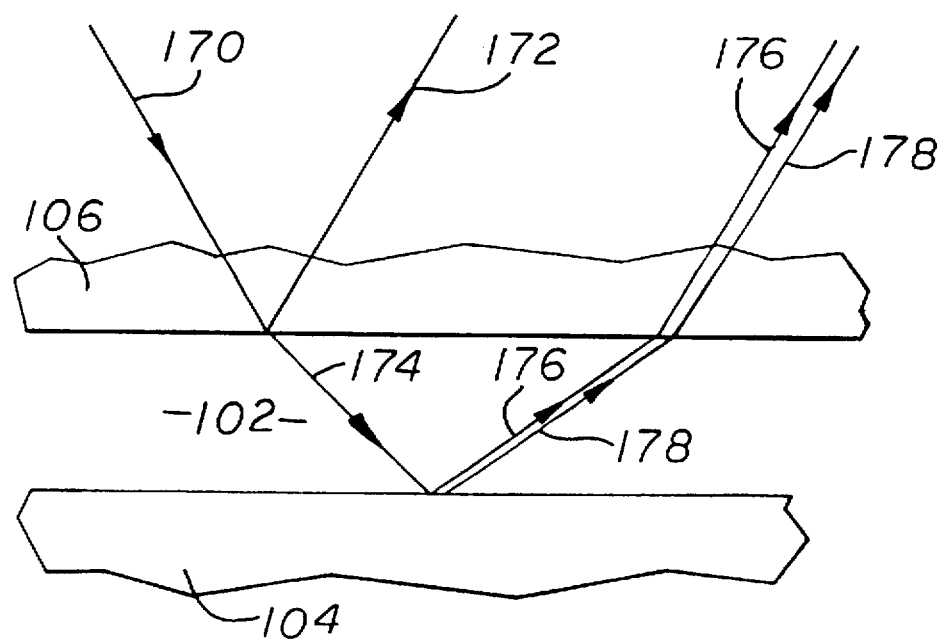
FIG. 5 is an enlarged view showing a light beam reflected from a slider-substrate interface.

FIG. 5 is a schematic of a glass-air-slider interface. The incoming beam 170 reaches the glass-air interface, originating a reflected beam 172 and a transmitted beam 174. The transmitted beam 174 travels through the air gap and reflects off of the slider surface, originating two beams 176 and 178. Beam 176 represents the fraction of light that retains the polarization information, and thus interferes with beam 172. Beam 172 is the light portion that is depolarized, and does not interfere with beam 172. Depolarization ratio d is defined as the ratio between the intensities of beams 178 and 174. The schematic in FIG. 5 is in reality oversimplified, and disregards multiple reflected beams. Multiple reflection effects are fully taken into account in the theory for the polarized beams, but are neglected for the depolarized ones since their contribution is not significant. It has been found that diffuse scattering and diffraction are frequently encountered when measuring sliders. The tester of the present invention measures all four stokes parameters to accurately determine the polarization state of the reflected light beam.

As one embodiment, the mueller matrix of the smooth interface can be replaced by a mueller matrix that accounts for the depolarization of reflected light. This new matrix, when applied to the stokes vector that represents the incoming beam will result in a stokes vector that is not completely polarized, i.e. $S_0^2 > S_1^2 + S_2^2 + S_3^2$. The apparent depolarization of this beam (as measured by $(S_0^2 - (S_1^2 + S_2^2 + S_3^2))/S_0^2$), however, will in general be larger than d, and will depend on flying height, since the overall intensity is a function of flying height while the depolarized fraction is not. When performing a flying height measurement, there is now an additional parameter d to be fit. This parameter is well constrained by the wealth of data points at different flying heights, and does not introduce ambiguity in the fits. There is related scattering of the reflected beam, that results in light traveling in directions other than along the reflection path. This light is thus not collected by the detector and its effect is accounted for in a similar fashion as the depolarized light. In general the tester equates a function that is dependent upon n, k, t and d with a function that is dependent upon all four stokes parameters $S_0$, $S_1$, $S_2$ and $S_3$, and utilizes this equality to determine n, k and the air bearing thickness t.

The tester 100 may have a second optical system 200 that detects a second light beam 202 reflected from the substrate 106 and the slider 104. The second light beam 202 is generated by a second light source 204 such as a quartz halogen lamp. Lenses 206 and 208, and beam splitter 210 direct the light beam 202 into the substrate 106 and the slider 104 at a normal incidence.

A portion of the light is reflected from the substrate 106 and another portion of the light is reflected from the slider 104. The reflected light creates an interference pattern. The second optical system 200 contains a detector 212 which detects the light intensities of the interfering light. In the preferred embodiment, the detector 212 is a three CCD chip solid state color camera. The detector 212 is coupled to the computer 156. The computer 156 can calculate the thickness of the air gap, with the intensities sensed by the detector 212, and the real index n and coefficient k computed from the first optical system 101, with the following equations.

$$\frac{I_{out}}{I_{in}} = \frac{r^2 + s^2 + 2rs\cos\left(\frac{4\pi H}{\lambda} - \Phi\right)}{1 + r^2 s^2 + 2rs\cos\left(\frac{4\pi H}{\lambda} - \Phi\right)}$$

where:

r=amplitude reflection off of glass substrate.
s=amplitude reflection off of slider.
λ=wavelength of illuminating light.
H=thickness of the air gap.
Φ=phase offset on reflection.

The variable r is calculated from the known refractive index of the glass die by $$r = \frac{n-1}{n+1}.$$

At a maximum of the interference pattern, the cos term is +1. Then s can be calculated from reflectively $$\frac{I_{out}}{I_{in}}\bigg|\text{max}.$$

The phase offset Φ is equal to 180 degrees if the slider material is a dielectric, wherein the material is transparent and light passes through with negligible loss. If on the other hand, the slider is not transparent, K differs from zero and the phase offset is calculated from the following expression.

$$\Phi = \tan^{-1}\frac{2n_0 k_1}{n_0^2 - n_1^2 - k_1^2}$$

where;

$n_1$=the real index of refraction of the slider or substrate;
$k_1$=the extinction coefficient of the slider or substrate; and,
$n_0$=the refractive index of the gap medium located immediately between the slider and substrate, usually air.

Given r, s and Φ a measured value of $$\frac{I_{out}}{I_{in}}$$

can be used to solve for the thickness H of the air gap.

In operation, the first 101 and second 200 optical systems detect the first 110 and second 202 light beams reflected from the substrate 106 and the slider 104. The first optical system can be used to compute the real index of refraction n and the extinction coefficient k of the slider 104. The relatively wide beam spot of the first light beam 101 provides a number of data points that are used to compute n and k. The second light beam 202 is directed at a normal angle and detected by a high speed image detector. Consequently, the image of the slider/substrate interface measured by the second optical system 200 has a higher resolution and a manageable number of data points that can be used to dynamically compute the air bearing thickness while the slider 104 is flying below the substrate 106. The tester 100 of the present invention can therefore provide n and k values for each slider and dynamically compute the gap of the air bearing. Alternatively, the second light beam 202 may have a relatively small spot diameter that can be rapidly detected by the detector to provide dynamic air bearing data.

What is claimed is:

1. An apparatus for measuring a space between a transparent member and a reflective member that has an index of refraction, comprising:

a first optical system that detects a first light beam that is reflected from the transparent member and the reflective member;

a second optical system that detects a second light beam that is reflected from the transparent member and the reflective member at an angle that is substantially normal to the transparent member, said second light beam having a spot diameter that is less than a spot diameter of said first light beam; and, a processor that computes the index of refraction of the reflective member from the detected reflected first light beam and computes the space from the computed index of refraction and the detected reflected second light beam.

2. The apparatus as recited in claim 1, wherein said first optical system splits the reflected first light beam into four separate reflected light beams.

11

3. The apparatus as recited in claim 2, wherein said processor computes a first stokes parameter, a second stokes parameter, a third stokes parameter, and a fourth stokes parameter from the four reflected light beams and computes the index of refraction from said first, second, third and fourth stokes parameters.

4. The apparatus as recited in claim 1, wherein said first optical system includes a photodetector that detects an image of the reflective member.

5. The apparatus as recited in claim 1, wherein said second optical system includes a photodetector that detects an image of the reflective member.

6. The apparatus as recited in claim 1, further comprising a calibration medium, wherein said first optical system is calibrated by reflecting the first light beam from said calibration medium.

7. A method for measuring a space between a transparent member and a reflective member that has an index of refraction, comprising the steps of:

a) reflecting a first light beam from the transparent member and the reflective member;

b) detecting the reflected first light beam;

12 c) reflecting a second light beam from the transparent member and the reflective member, at an angle that is substantially normal to the transparent member, said second light beam having a spot diameter that is less than a spot diameter of said first light beam;

d) detecting the reflected second light beam;

e) computing the index of refraction from the detected reflected first light beam; and, f) computing the space from the computed index of refraction and the detected reflected second light beam.

8. The method as recited in claim 7, further comprising the step of splitting the reflected first light beam into four separate light beams.

9. The method as recited in claim 8, further comprising the steps of computing a first stokes parameter, a second stokes parameter, a third stokes parameter, and a fourth stokes parameter, and computing the index of refraction and the space from the first, second, third and fourth stokes parameters.

10. The method as recited in claim 7, wherein an image of the reflective member is detected.

* * * * *